(12) United States Patent
Baaijens et al.

(10) Patent No.: US 9,109,310 B2
(45) Date of Patent: Aug. 18, 2015

(54) MULTILAYER PREFORM OBTAINED BY ELECTRO-SPINNING, METHOD FOR PRODUCING A PREFORM AS WELL AS USE THEREOF

(75) Inventors: Franciscus Petrus Thomas Baaijens, Waalre (NL); Mirjam Petronella Rubbens, Eindhoven (NL); Martijn Antonius Johannes Cox, Eindhoven (NL)

(73) Assignee: Technische Universiteit Eindhoven, Eindhoven (NL)

( * ) Notice: Subject to any disclaimer, the term of this patent is extended or adjusted under 35 U.S.C. 154(b) by 498 days.

(21) Appl. No.: 13/122,387

(22) PCT Filed: Oct. 9, 2009

(86) PCT No.: PCT/NL2009/050611
§ 371 (c)(1),
(2), (4) Date: Jun. 10, 2011

(87) PCT Pub. No.: WO2010/041944
PCT Pub. Date: Apr. 15, 2010

(65) Prior Publication Data
US 2011/0250689 A1    Oct. 13, 2011

(30) Foreign Application Priority Data

Oct. 9, 2008 (NL) .................................... 1036038

(51) Int. Cl.
| | |
|---|---|
| *A61F 2/24* | (2006.01) |
| *D04H 1/42* | (2012.01) |
| *D01D 5/00* | (2006.01) |
| *D04H 1/728* | (2012.01) |
| *D04H 13/00* | (2006.01) |

(52) U.S. Cl.
CPC ............... *D04H 1/42* (2013.01); *D01D 5/0076* (2013.01); *D04H 1/728* (2013.01); *D04H 13/00* (2013.01); *A61F 2/24* (2013.01); *A61F 2/2418* (2013.01); *Y10T 428/2913* (2015.01)

(58) Field of Classification Search
CPC .................................. A61F 2/24; A61F 2/2418
USPC ......................................................... 435/398
See application file for complete search history.

(56) References Cited

U.S. PATENT DOCUMENTS

| | | | |
|---|---|---|---|
| 4,043,331 A | | 8/1977 | Martin et al. |
| 2006/0194036 A1 * | | 8/2006 | Miyamoto et al. ......... 428/313.3 |
| 2007/0274862 A1 * | | 11/2007 | Harttig ............................. 422/56 |
| 2007/0275034 A1 * | | 11/2007 | Shalaby et al. ............... 424/423 |
| 2008/0112998 A1 | | 5/2008 | Wang |
| 2008/0131965 A1 | | 6/2008 | Baaijens et al. |

FOREIGN PATENT DOCUMENTS

WO    03045875 A    6/2003

OTHER PUBLICATIONS

International Search Report for PCT application PCT/NL2009/050611 of which the instant U.S. application is a National Phase.

* cited by examiner

*Primary Examiner* — Ruth Davis
(74) *Attorney, Agent, or Firm* — Lumen Patent Firm (57) ABSTRACT

The invention relates a multilayer preform obtained by electro-spinning, which preform is suitable as a scaffold for a prosthesis, which preform comprises at least one layer of microfibers and at least one layer of nanofibers, wherein the pore size of the at least one layer of microfibers is in the range of 1-300 micrometer and in that the pore size of the at least one layer of nanofibers is in the range of 1-300 micrometer. The present invention also relates to a method of producing said preform. The present invention also relates to the use of the present preform as a substrate for growing human or animal tissue thereon. The present invention furthermore relates to a method for growing human or animal tissue on a substrate, wherein the present preform is used as the substrate.

6 Claims, 6 Drawing Sheets

| Fiber diameter [μm] | Poresize [μm] | Microscopic appearance | Cell in-growth visualization | Cell in-growth qualification |
|---|---|---|---|---|
| < 1 | <10 | N.A. | N.A. | Impossible |
| 3.4 | ~15 |  |  | Poor/ Impossible |
| 5.0 | ~22 |  |  | Poor |
| 6.7 | ~27 |  |  | Reasonable |
| 8.7 | ~35 |  |  | Good |
| 12.1 | ~50 |  |  | Good |
| > 30 | >200 | N.A. | N.A. | Poor; difficult to retain cells |

FIG. 8

MULTILAYER PREFORM OBTAINED BY ELECTRO-SPINNING, METHOD FOR PRODUCING A PREFORM AS WELL AS USE THEREOF

The present invention relates to a multilayer preform obtained by electro-spinning, which preform is suitable as a scaffold for a prosthesis, which preform comprises at least one layer of microfibres and at least one layer of nanofibres. The present invention moreover relates to a method for producing a preform by means of electro-spinning. In addition, the present invention relates to the use of such a preform and to a method of growing human or animal tissue on a substrate.

The publication of Q. P. Pham et al. in Biomacromolecules 2006, Vol. 7, pp. 1796-1805 relates to a electro-spun multilayer preform based on polymer fibres of ϵ-polycaprolactone. The multilayer preform comprises alternating layers of microfibres having a diameter of 2 to 10 micrometer and nanofibres having a diameter of approximately 600 nanometer. However, ingrowth of cells into the preform matrix is not optimal due to non-optimal passage of cells and nutrients into the preform.

U.S. 2008/112998 relates to a synthetic tissue scaffold comprising alternating layers of electrospun polymers and mammalian cells sandwiched within. The presence of mammalian cells in tissue scaffolds complicates sterilization and storage of the scaffold prior to use.

US 2008/0131965 corresponding to NL 1026076 discloses a method for producing a preform by means of an electro-spinning process. It does not relate to a method for producing a preform from nano and micro fibers.

An object of the present invention is to provide a preform from which three-dimensional prostheses or implants can be produced.

Another object of the present invention is to provide a preform having excellent ingrowth of cells.

Another object of the present invention is the provision of a preform having an optimal balance between structural and mechanical stability on the one hand and ingrowth and attachment of cells on the other hand.

In addition, it is an object of the present invention to provide a preform that can be used as a substrate for growing human or animal tissue.

It is moreover an object of the present invention to provide a substrate for a prosthesis or an implant, in particular for a heart valve, a blood vessel, a T-connection for connecting blood vessels, or a cardiac patch.

One or more of the above objects are realized by a multilayer preform according to the preamble, characterized in that the pore size of the at least one layer of microfibres is in the range of 1-300 micrometer and in that the pore size of the at least one layer of nanofibres is in the range of 1-300 micrometer.

In an embodiment of the present invention the pore size of all layers in the preform, i.e. the pore size of the complete network of fibers or the preform, is in the range of 1-300 micrometer. In this way the porosity of the total preform is in the desired range allowing optimal infiltration of cells and nutrients throughout the total thickness of the preform.

The present inventors have found that when using a preform based on one or more layers of microfibres combined with one or more layers of nanofibres it is essential that the pore size of the one or more layers of microfibres as well as the one or more layers of nanofibres is sufficiently large to insure good ingrowth of cells as well as good diffusion of nutrients.

After elaborate research the present inventors have found that an optimal balance between structural and mechanical properties on the one hand and ingrowth and attachment of cells on the other hand can be obtained by a preform according to the present invention. In particular, the pore size of the layer of nanofibres was found by the present inventors to be critical and without wanting to be bound to a specific theory the present inventors are of the opinion that the pore size of the layer(s) of nanofibres is responsible for sufficient ingrowth of cells.

BRIEF DESCRIPTION OF THE DRAWINGS

The present invention is best understood from the following detailed description when read with the accompanying drawings.

DETAILED DESCRIPTION

The term 'microfibres' as used in the present specification means fibres having a diameter in the micrometer range.

The term 'nanofibres' as used in the present specification means fibres having a diameter in the nanometer range.

The term 'preform' as used in the present specification means an article having a three dimensional form which may be used as a scaffold for tissue engineering.

The term 'multilayer' as used in the present specification means comprising at least two layers, one of nanofibers and one of microfibers. Included in this definition in the scope of the present invention are gradient layered preforms which are built up of a infinite number of very thin layers one on top of the other, wherein the diameter of the fibers changes continuously going from one layer to another layer. This can for example in electro-spinning be achieved by continuously changing the spinning parameters during the spinning operation whereby the diameter of the fiber increases or decreases continuously. A very basic example of a gradient multilayered preform is a preform having on one outer surface a microfiber layer and on the other outer surface a nanofiber layer and in between are an infinite number of microfiber layers and nanofiber layers one on top of each other each having a smaller diameter than the layer before.

It is known to use electro-spinning in the manufacturing of so-called scaffolds which are used in the field of tissue engineering. In the electro-spinning process many parameters can be changed that alter and optimize properties of the desired scaffold, making electro-spinning a versatile technique. Examples of applications for electro-spun preforms are the use as scaffolds or moulds for tissue engineering, as drug delivery devices and as wound dressings.

In Dutch patent NL 1026076 (corresponding to US 2008/0131965) of one of the present inventors a method is disclosed for the preparation of preform by means of electro-spinning of polymer microfibres, which preform can be used as a scaffold for a prosthesis of a heart valve. The moulds and submoulds as disclosed in FIGS. 3-7 are disclosed in the Dutch patent.

Electro-spinning is a technique using a metal target or mould, having either a flat, plate-like form or a complex three-dimensional form, depending of the preform that is desired. Polymer fibres are deposited onto this mould by means of an electromagnetic field. The polymer fibers are generated from a solution of one or more polymers in one or more solvents. This technique of electro-spinning is known per se and will not be further in detail in this specification.

Any fibre material that can be processed by electro-spinning can be used as the material for the fibre layers according to the present invention. It is preferred however in the present invention to use polymeric materials, in particular biologically compatible polymeric materials, as the fibre material. Examples of suitable polymers are mentioned hereafter.

After the fibres have been deposited onto the surface of the (sub)mould, the (sub)mould is removed from the fibres and a preform or scaffold of fibres is obtained. This preform is a very porous network of non-woven, overlapping fibres which can be used as a substrate for the ingrowth and growth of cells and tissue. Infiltration of the cells and tissue formation can take place either in vivo or in vitro. For in vivo tissue formation, an unseeded or seeded preform—i.e. a preform with is or is not seeded with cells—is implanted in the body and attracts cells and promotes tissue formation. For in vitro tissue formation the preform is incubated using human or animal cells, which are able to grow in the open fiber-like structure. Said incubation can be carried out under suitable conditions of availability of nutrients and growth factors, temperature, time, pH, mechanical and biochemical stimuli and the like so as to optimise the cell growth. This leads to tissue formation in and on the preform. This combination of tissue and preform can be used as an implant or prosthesis. The prosthesis or implant thus obtained can be implanted into a human or animal body.

If biodegradable polymer is used for the fibers layers to prepare a preform according to the present invention, the porous fibrous network of the scaffold is degraded either during the tissue growth in vitro or after implantation in vivo or both. As a result only the newly formed tissue remains which forms a natural prosthesis. Hence it is preferred according to the present invention to use a biodegradable or biologically absorbable polymer for the preform, ensuring nearly complete degradation or resorption of the preform after a certain amount of time; the polymeric material being replaced by human or animal tissue, leaving a completely natural implant or prosthesis to be present in the body.

The electro-spun scaffolds are characterized by several important parameters. A first parameter is the fiber diameter, which is for example measured by means of electron microscopy. The fiber diameter can have an effect on several properties of the scaffold, such as the surface area and the parameters mentioned hereafter. The present invention requires the presence of at least two layers having different fiber diameters, namely at least one layer having microfibres and at least one layer having nanofibres.

A second parameter is the pore size of the scaffold, measured for example by means of mercury porosimetry. The pore size of the layers of the present preform should be between 1 and 300 micrometer.

A third parameter is porosity, measured for example by mercury porosimetry, fluid intrusion and gravimetry. The pore size and porosity are critical properties of a scaffold that influence the attachment, proliferation, migration and/or differentiation of cells.

The use of layers of microfibres ensures good structural and mechanical stability of the fibrous scaffold. The use of layers of nanofibres ensures good compatibility with human and/or animal cells, which cells are being used to grow tissue in the scaffold. The present inventions have found that a combination of both within a specific pore size ranges provides an optimal balance between structural and mechanical stability on the one hand and good compatibility with human and/or animal cells on the other hand.

The ECM is the extracellular matrix, being the extracellular part of human or animal tissue that provides structural support to cells. The ECM is constituted of the interstitial matrix and the base membrane. The interstitial matrix is present in between different cells and is formed by a gel of polysaccharides and fibrous proteins (which show physical resemblance to the present nanofibres). Base membranes are sheet-like depositions of ECM onto which epithelial cells attach and grow. The layers of nanofibres as used in the present invention mimic the physical characteristics of the extracellular matrix of a cell. The advantages of this mimicry is that cells that are grown onto the preform are comfortable in their surroundings and hence show and excellent attachment to the layer(s) of nanofibres; which attachment is better than the attachment of the same cells to layer(s) of microfibres. A number of preferred embodiments for the preform are defined in the subclaims and will be explained in more detail hereinafter.

In one embodiment of the present invention the pore size of the at least one layer microfibres is between 1 and 300 micrometer. The maximum pore size is preferably 250 micrometer, more preferably 200 micrometer. In an even more preferred embodiment the pore size is between 5 and 100 micrometer. The most preferred pore size is dependent on the type of cells to be cultured and is between 5 and 50 micrometer for animal cells and between 20 and 100 for human cells.

In one embodiment of the present invention the pore size of the at least one layer nanofibres is between 1 and 300 micrometer. The maximum pore size is preferably 250 micrometer, more preferably 200 micrometer. In an even more preferred embodiment the pore size is between 5 and 100 micrometer. The most preferred pore size is dependent on the type of cells to be cultured and is between 5 and 50 micrometer for animal cells and between 20 and 100 for human cells.

In one embodiment of the present invention the pore size of all layers of the preform, i.e. the pore size of the complete network of fibers or the preform, is between 1 and 300 micrometer. The maximum pore size is preferably 250 micrometer, more preferably 200 micrometer. In an even more preferred embodiment the pore size is between 5 and 100 micrometer. The most preferred pore size is dependent on the type of cells to be cultured and is between 5 and 50 micrometer for animal cells and between 20 and 100 for human cells.

The advantage of these pore sizes of the layer of microfibres as well as nanofibres is that it allows the passage of the cells to be cultured and hence a good infiltration of cells into the complete thickness of the preform, which is required to ensure formation of tissue throughout the complete preform. The pore size depends on the size of the cells to be cultured and can be selected according to this size. The size of human cells in generally larger that the size of animal cells, hence the differentiation between the most preferred pore sizes when using either animal or human cells.

In another embodiment of the present invention, the diameter of the microfibres is in the range of 3-20 micrometer, preferable 5-18 micrometer and in particular 8-14 micrometer, for example approximately 12 micrometer. The advantage of this diameter is the excellent mechanical and structural stability.

Figure 8:
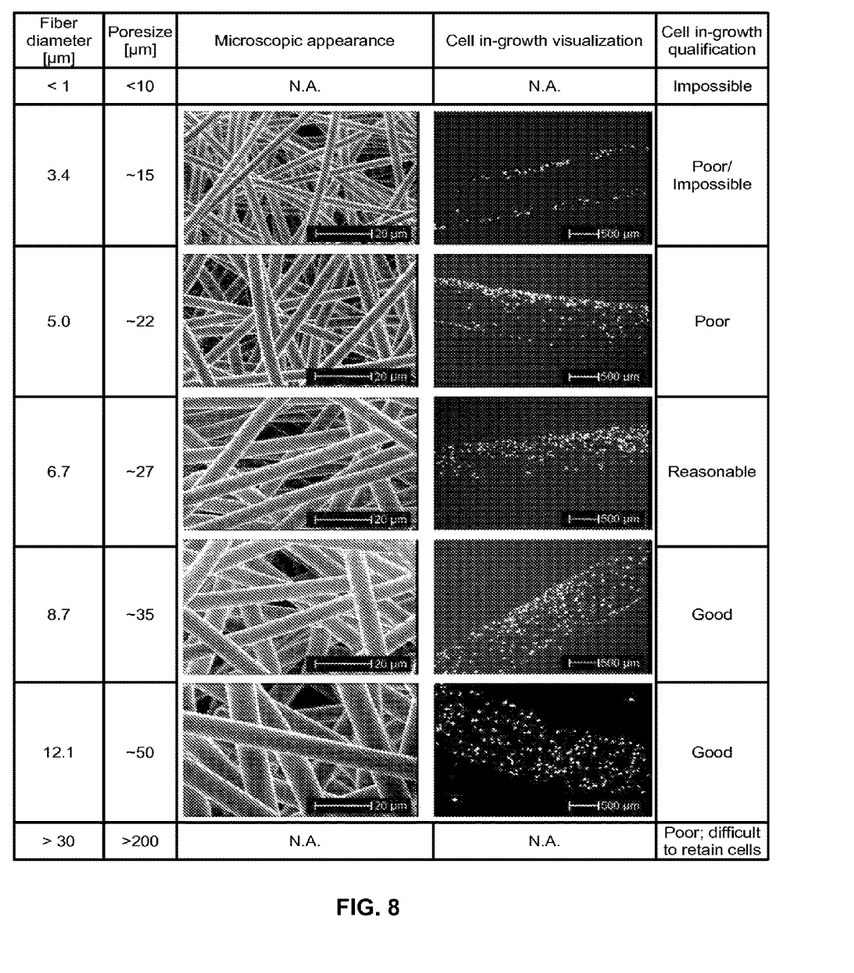
FIG. 8 discloses information about several microfibers used in the present invention.

FIG. 8 gives an overview of several types of microfibers to be used in the present invention.

FIG. 8 shows in the first column the fiber diameter in micrometer. The second column shows the pore size in micrometer for a layer of these fibers. The third column shows photos of the microscopic appearance of the layer of fiber. The fourth column shows photos of the cell in-growth visualisation and the fifth and final column shows the cell in-growth qualification.

Although only microfibres are used in this graph, the effect of pore size on cell in-growth is clearly demonstrated. Visualization data are adapted from FIG. 4.1 of Balguid, Strategies to optimize engineered tissue towards native human aortic valves, PhD thesis Eindhoven University of Technology, 2008. The pore size-estimated by combining aforementioned data with FIG. 4 in Pham et al. mentioned previously. The present method will enable the present inventor to decouple the relationship between fiber diameter and pore size, which allows sufficient cell in-growth even at nano-fiber scale.

In another embodiment of the present invention, the diameter of the nanofibres is in the range of 50-800 nanometer, preferable 100-800 nanometer, more preferably 200-800 nanometer and in particular 400-800 nanometer which mimics the nanoscale dimensions of the ECM. In other embodiments the maximal diameter of the nanofibres may be 700 nanometers or even 600 nanometers.

In another embodiment of the present invention the porosity of the at least one layer of microfibres is in the range of 70-95%.

In another embodiment of the present invention the porosity of the at least one layer of nanofibres is in the range of 70-95%.

The advantage of this range of porosity for the layer of microfibres and the layer of nanofibres is that it allows the passage of the cells to be cultured and hence a good infiltration of cells into the complete thickness of the preform, which is required to ensure formation of tissue throughout the complete preform. The pore size depends on the size of the cells to be cultured and can be selected according to this size.

The present preform may be constructed from one single layer of microfibres and one single layer of nanofibres. In this case the layer of microfibres may be present as the inner or as the outer layer.

In addition, the present preform may be constructed from two layers of microfibres sandwiching a layer of nanofibres or vice versa.

Moreover, it is also possible to construct the present preform from any number of layers of microfibres and any number of layers of nanofibres, either alternating or in any other desired configuration, for example a large number of layers having increasing diameters or even a gradient multilayer having a very large or even infinite number of layers having diameters increasing from a nanofiber layer to a microfiber layer or vice versa or from a nanofiber layer to a microfiber layer and back to a nanofiber layer or vice versa.

In one embodiment of the present invention mammalian cells are not incorporate in the scaffold during production of said scaffold. The absence of mammalian cells allows for easy storage and sterilization of the scaffold prior to use. Another advantage of the scaffold according to the present invention is that cells of choice can be seaded on the scaffold prior to use. Scaffolds already comprising mammalian cells can only be used for the cells present in the scaffold.

Figure 1:
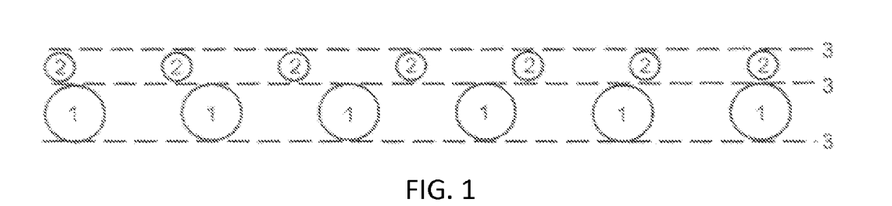
FIG. 1 discloses a schematic cross section of a two-layer preform according to one embodiment of the present invention.
Figure 2:
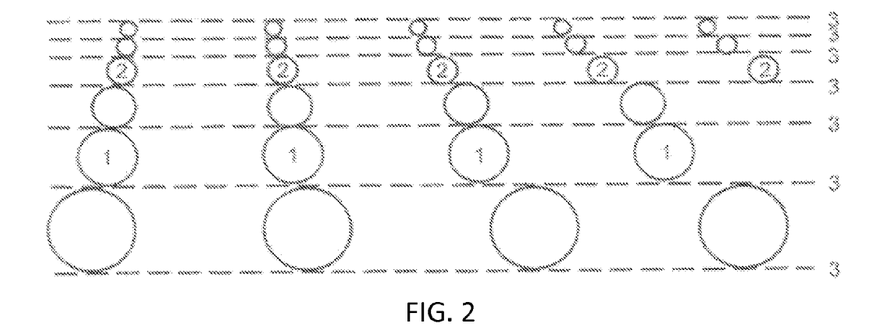
FIG. 2 discloses a schematic cross section of a gradient layered preform according to another embodiment of the present invention.
Figure 3:
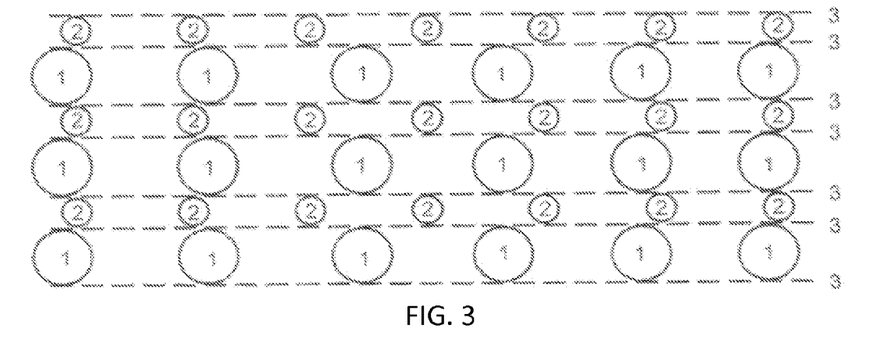
FIG. 3 discloses another embodiment of the multilayer preform according to the present invention.

FIGS. 1, 2 and 3 give very schematic representation of three possible embodiments of a multilayer preform according to the present invention. The drawings are not drawn to scale.

FIG. 1 discloses a schematic representation of a cross section of a two layer preform. A first layer of microfibres 1 and a second layer of nanofibres 2. The dotted lines 3 give the boundaries of these layers. In this embodiment the layers are planar and there is no overlap between the layers. In addition, the pore size for both layers is similar.

FIG. 2 discloses a gradient multilayer with six layers having different fiber diameters ranging from nanofibres to microfibres. Again the dotted lines give an indication of the boundaries between the layers. Again the pore size for the layers is similar.

FIG. 3 discloses an alternating multilayer having three layers of microfibres 1 and three layers of nanofibres 2. Again the dotted lines give an indication of the boundaries between the layers. Again the pore size for the layers is similar.

A preform according to the present invention can show layers that are less planar and wherein the boundary between the separate layers is less defined.

The thickness of a layer of microfibres is for example between 10 and 500 micrometer, preferably between 50 and 250 micrometer.

The thickness of a layer of nanofibres is for example between 100 nanometer and 500 micrometer, preferably between 10 and 250 micrometer.

The thickness of the total preform is preferably between 300 and 1000 micrometer for a heart valve, between 300 and 1000 for a blood vessel and between 500 and 2000 for a cardiac patch. Other thickness can be determined by a skilled person depending on the use.

The thickness of the layer(s) or microfibres and layer(s) of nanofibres depends on the application. In an application requiring strong mechanical properties the thickness of the layer(s) of microfibres will in general be larger than in an application required less strong mechanical properties. In addition there is also a relation to the pore size of the different layers. For example, when the pore size is larger the layers can be thicker and still maintain the same ease of infiltration. The different parameters are hence closely related and can be tuned with respect to each other for each specific application within the claimed ranges by a person skilled in the art without undue burden.

The thickness of the total preform also depends on the application. In an application requiring strong mechanical properties the total thickness of the preform will in general be larger than in an application required less strong mechanical properties.

With the use of electro-spinning a polymer preform or scaffold is obtained. A polymer scaffold would overcome the shortcomings of currently engineered cardiovascular tissues, being the lack of elastin. Proper in vivo functioning of vascular tissue engineered grafts has been unsuccessful due to the lack of elastin biosynthesis in the tissue equivalents. Polymeric scaffolds exhibit however elastic behaviour with only minor permanent deformation. Therefore polymers, such as for example polycaprolactone, could function as an elastic substitute while natural elastin is gradually produced to take over this role.

The polymer that is used to obtain the present electro-spun preform is not limited and can be selected by a person skilled in the art according to the requirements of each specific use. Examples of suitable polymers are aliphatic polymers, copolyesters, polyhydroxyalkanoates and polyalkyleneglycol, e.g. poly-ethyleneglycol, polycaprolactone.

It is preferred that the polymer used in the process or electro-spinning is biodegradable or biologically absorbable.

It is also possible that mixtures of two or more polymers are used. In addition, it is possible to use block co-polymers, comprising two or more blocks. It is for example possible to use blocks of polymers having mutually different decomposition rates.

In a specific embodiment of the present invention, at least two fibre layers (either microfibres, nanofibres or a combination) have mutually different biological decomposition rates. Said decomposition rate can be measured in accordance with standard methods, which will not be explained in more detail herein. Either the biological decomposition of the inner fibre layer takes place more rapidly than that of the outer fibre layer. In this way the outer fibre layer provides the required strength, whilst the inner fibre layer can be quickly substituted for natural tissue. Or the biological decomposition of the outer fibre layer takes place more rapidly than that of the inner fibre layer. In this way the inner fibre layer provides the required strength, whilst the outer fibre layer can be quickly substituted for natural tissue.

Another especially preferred embodiment relates to the use of a fibre layer (either microfibres or nanofibres or both) comprising fibres composed of at least two components, wherein the various components have mutually different biological decomposition rates as mentioned above. The fibre consists of sequentially arranged component a and component b, for example, so that a fibre exhibiting a repetitive composition -a-b-a-b-a-b- is obtained. When such a fibre layer is used, one of the two components will decompose after some time, so that a collection of short fibres remains, viz. the fibres of the component having the slower decomposition rate. The short fibres, which are still present, contribute to the mechanical strength of the newly formed natural tissue, whilst the tissue can grow, which is not possible when a fibre layer that only consists of a slowly decomposing component is produced. An advantage of the use of a fibre layer consisting of fibres that are composed of two components is the fact that when a preform made of such fibres is used for implantation into young patients, no subsequent surgery is required for exchanging the implant for a larger implant. After all, the implant produced in accordance with the present invention can grow with the patient. However, this advantage can also be achieved by other embodiments of the present invention.

The present invention furthermore relates to a method of producing a preform by means of electro-spinning, which preform is suitable for use as a scaffold for a prosthesis, characterized in that the method comprises the steps of providing a mould and subsequently applying, in random order, by means of electro-spinning at least one layer of microfibres and at least one layer of nanofibres, in which the pore size of the at least one layer of microfibres is in the range of 1-300, preferably 5-100 micrometer and the pore size of the at least one layer of nanofibres is in the range of 1-300, preferably 5-100 micrometer.

The present inventors have developed the above method which makes is possible to obtain a preform that allows for sufficient infiltration of cells as well as sufficient diffusion of nutrients for the growing tissue. The manufacturing of layers of nanofibres having a pore size in the range of 1-300, preferably 5-100 micrometer has not been carried out up until now.

A number of preferred embodiments for the method are defined in the subclaims and will be explained in more detail hereinafter. The embodiments described for the preform are also applicable to the method and vice versa.

In one embodiment of the present method the step of electro-spinning of the at least one layer of nanofibres and possibly the at least one layer of microfibres is carried out at a temperature below 220 K (−53° C.) for example in the range of 200 to 220 K (−73° C. to −53° C.) as disclosed in the publication of Simonet et al. Polymer engineering and science, 2007, pages 2020-2026. Temperatures lower than 200 K may also be used depending on the method used for cooling, which may for example be dry ice or liquid nitrogen. This process of electro-spinning at low temperature is called cryo electro-spinning. The advantage of the use of such low temperature is that it allows the formation of micrometer dimension pores. Not wishing to be bound by this theory, the present inventors believe this is caused by the formation of ice crystal caused by the freezing of water droplets that are present in the electro-spinning solution. These ice crystals are embedded in the porous network during electro-spinning of the nanofibres. After the process the temperature is brought back to room temperature and the ice crystals melt, leaving pores having a size in the diameter range.

In another embodiment the method comprises the steps of providing a mould, electro-spinning at least one layer of nanofibres and subsequently providing at least one layer of microfibres.

In another emobidment no mammalian cells are incorporated into the preform during electro-spinning. The cells are only incorporated after the preform has completed.

The present invention also relates to the use of a preform obtained with the present method as a substrate for growing human or animal tissue therein.

The present invention furthermore relates to a method for growing human or animal tissue on a substrate, wherein the present preform is used as the substrate. In this way the preform obtained by electro-spinning can be provided with a layer of human or animal tissue.

In one embodiment the scaffold is for the preparation of a prosthesis for a hart valve. In another embodiment the scaffold is for the preparation of a prosthesis for a blood vessel or a connection of blood vessels. When one or more blood vessels are connected by suturing, leakage frequently occurs, because this is a complex procedure and the blood vessels are so small and circular in shape that suturing is problematic. Consequently, there is a need for a T-connection that can be used for connecting two or more blood vessels.

The present invention is in particular suitable for the preparation of preforms by electro-spinning which preforms have a complex three-dimensional shape. In particular, the present invention is suitable to prepare a preform according to Dutch patent NL 1026076 which preform can be used as a scaffold for a prosthesis of a heart valve.

The human heart performs an impressive biomechanical task, beating 100,000 times and pumping 7,200 liters of blood through the body each day. This task results in large mechanical loads, especially on the aortic heart valve, which rise up to 80 mmHg during the diastolic phase. The native valve leaflets have an anisotropic collagen architecture with a preferential fiber alignment in the circumferential direction, resulting in minimal resistance during systole, and sufficient strength and stiffness to accommodate diastolic loads. In (small diameter) arteries collagen is organized in a helical structure. Again nature has optimized this design for withstanding arterial pressures.

The mechanical demands for electro-spun scaffolds are accordingly challenging, especially when designed for a one-step approach. Scaffolds should be strong and durable, but also flexible to allow for: a) proper opening and closing in case of a heart valve, or b) elastic deformation following the deforming beating heart in case of a coronary artery or cardiac patch. Furthermore, diabetic shunts should allow for repeated puncturing for dialysis. Hemodynamic performance and durability requirements have been defined in ISO-norms for e.g. bioprosthetic heart valves with regards to effective orifice area, amount of regurgitation, mean and maximum systolic pressure gradients as well as durability [Norm EN ISO 5840: 2006 Cardiovascular Implants Cardiovascular prostheses].

Besides hemodynamic performance, scaffolds should provide the appropriate micro-mechanical environment to enable proper cellular differentiation or phenotype conservation and in-vivo tissue maturation. In addition, the scaffold should promote the formation of the collagen architectures found in heart valves and small diameter arteries. In our opinion, it is the specific combination of nano- and microfibers that we propose that can meet all the necessary requirements.

The present invention therefore also relates to a method for producing a preform by means of an electro-spinning process, comprising the steps of:

a) providing a mould made up of at least two submoulds, which submoulds substantially exclusively comprise convex surfaces;

b) applying at least one layer of nano or microfibers to the surface of at least one of the submoulds of step a) by electro-spinning;

c) combining at least two submoulds selected from the submoulds of step a) and the submoulds of step b);

d) applying at least one layer of nano or microfibers to the surface of the assembly of step c) by electro-spinning to obtain the preform, wherein the preform comprises at least one layer of nanofibers and at least one layer of microfibers, wherein the pore size of the at least one layer of microfibres is in the range of 1-300 micrometer and in that the pore size of the at least one layer of nanofibres is in the range of 1-300 micrometer.

The advantage of the this method is that it is possible to obtain a preform having any desired (complex) three-dimensional shape, using an electro-spinning process, by converting the intended three-dimensional shape into a mould, which mould is subdivided into a number of submoulds. Said submoulds have a spatial configuration such that, besides the usual flat parts, they substantially exclusively comprise convex surfaces.

When a fibre layer is applied to a target having a complex three-dimensional shape, viz. convex, concave and flat parts, by means of an electro-spinning process, problems occur in the forming of the fibre layer, since it appears not to be possible to form a uniform fibre layer because extra fibres are formed between the concave edges of the mould. Thus it is difficult to provide such concave surfaces with a uniform fibre layer, which uniform fibre layer is highly desirable in practice.

The aforesaid problem is solved by the steps a)-d) of the present method, in which the very presence of concave surfaces is avoided by subdividing the mould into a number of submoulds, which submoulds are so constructed that the submoulds do not have any concave shapes any more but substantially exclusively comprise convex surfaces besides the usual flat parts.

The various submoulds of which the mould is built up are so constructed that they can be combined to form the mould. The submoulds have one or more surfaces that are contiguous to one or more surfaces of the other submoulds, so that said submoulds fit together so as to jointly form the mould.

Since the preforms that are used in practice frequently have concave as well as convex surfaces, it has not been possible so far to produce such complex three-dimensional preforms provided with uniform fibre layers by coating the mould by means of an electro-spinning process.

It is possible to obtain the desired preforms by subdividing the mould into a number of submoulds, which submoulds each mainly comprise convex surfaces besides the usual flat parts that are already present. Subsequently, said submoulds can be separately provided with fibre layers in one or more steps, after which the submoulds provided with fibre layers can be joined together and as a whole be provided with an additional fibre layer so as to strengthen the whole.

The submoulds are made of a material that is suitable for use with electro-spinning, such as a metal.

The submoulds may be solid or partially hollow. If the submoulds are partially hollow, they may have a closed exterior surface. The submoulds or the mould may be provided with one or more openings, in which openings holders can be fitted, for example, which holders can be used for correctly positioning the submoulds or the mould during the electro-spinning process. Also other suitable materials can be used, however. Hollow submoulds or submoulds comprising channels or orifices can be used in order to allow the cooling of the submould for cryospinning conditions.

The fibre layers are applied to the surface of the submould/mould, which surface is understood to be the exterior surface of the submould/mould.

Figure 4A:
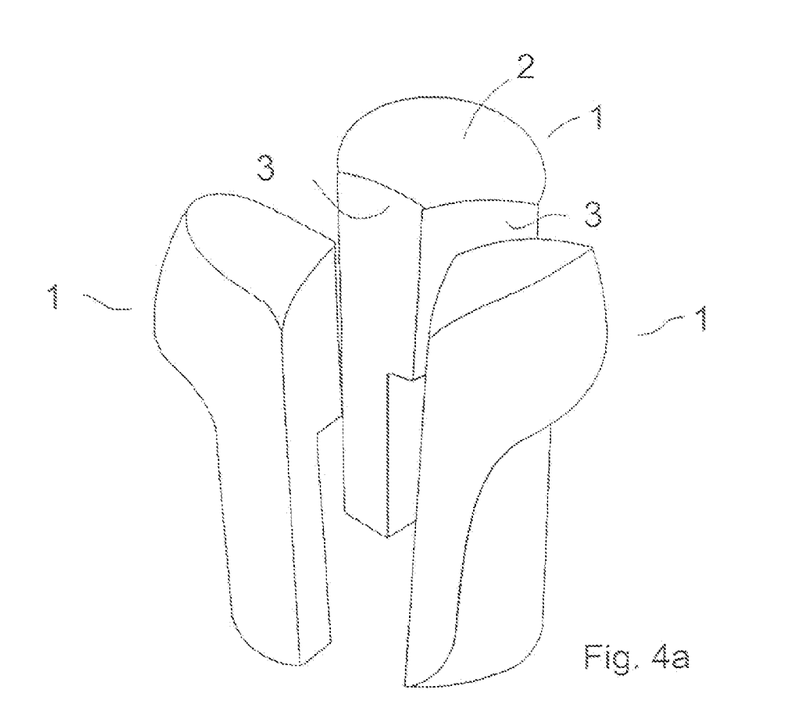
FIG. 4a shows three submoulds of a mould that can be used for the electro-spinning of a preform according to the present invention to be used as a scaffold for an artificial, three-membrane heart valve.
Figure 4B:
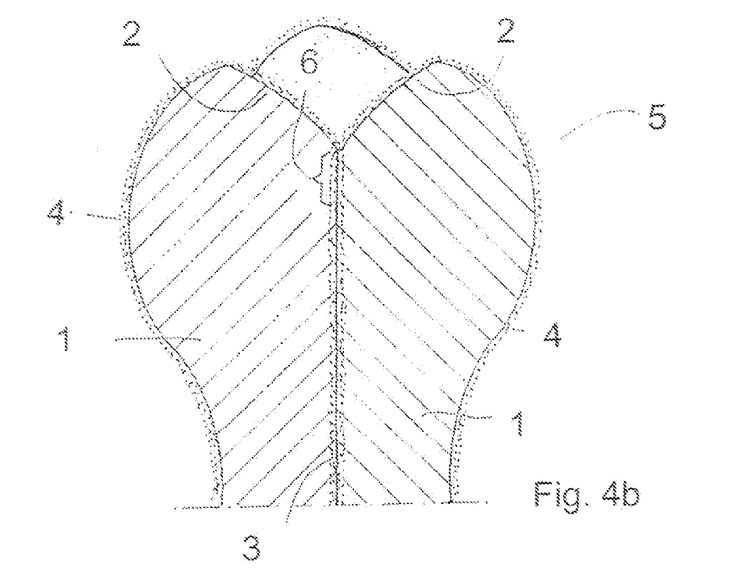
FIG. 4b is a sectional view of an assembly of the submoulds of FIG. 4a, which have been provided with one microfiber layer and one nanofiber layer by means of electro-spinning.
Figure 5A:
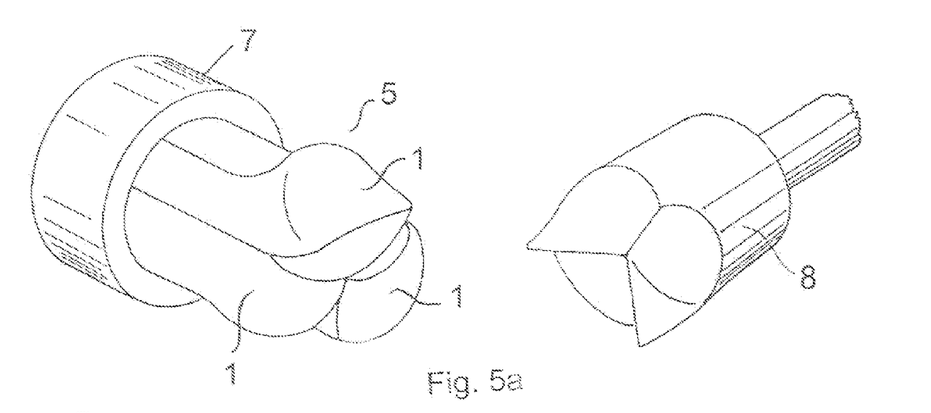
FIG. 5a shows an assembly of the three submoulds of FIG. 4a and a complementary submould for obtaining a complete heart valve, whilst
Figure 5B:
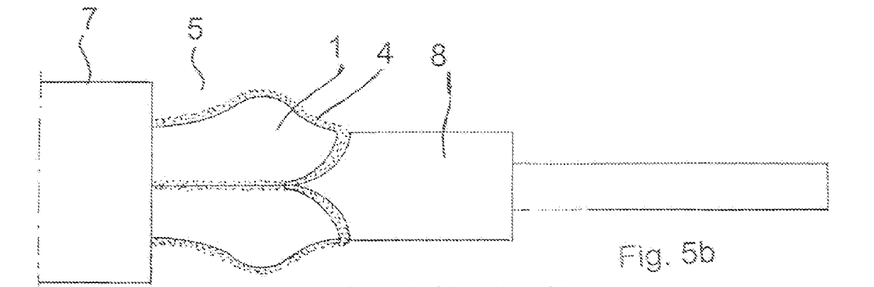
FIG. 5b is a sectional view of the submoulds of FIG. 5a slid one into another.
Figure 5C:
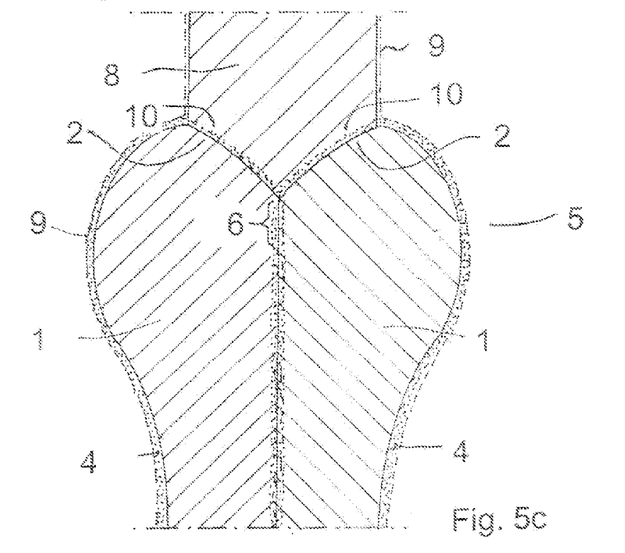
FIG. 5c is a sectional view of the entire mould for the heart valve comprising one microfiber layer and one nanofiber layer obtained after electro-spinning.
Figure 6A:
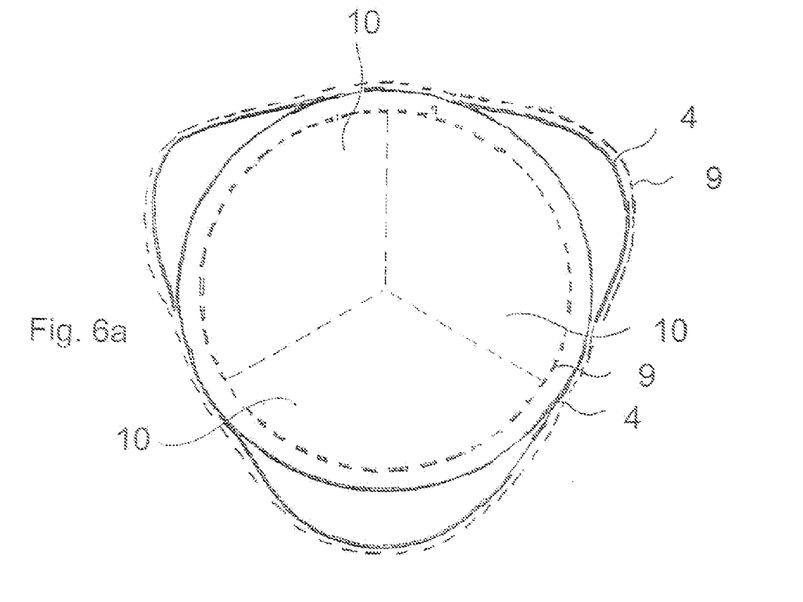
FIGS. 6a and 6b are a top plan view and a side view, respectively, of a preform according to the present invention obtained by using the mould of FIGS. 5a-5c.
Figure 6B:
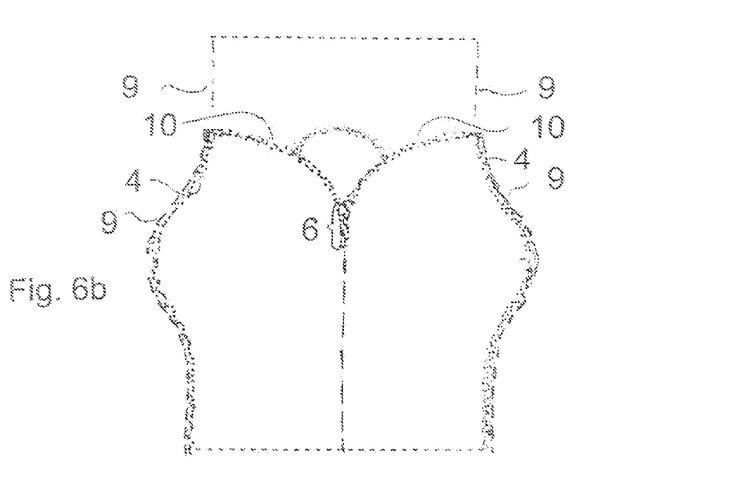
Figure 7A:
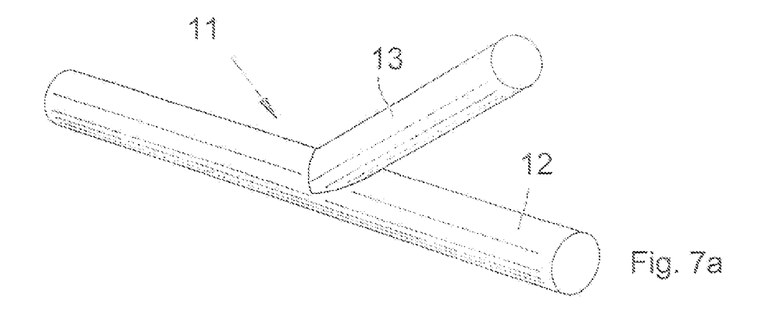
FIG. 7a shows a mould according to another embodiment of the present invention, a T-piece for connecting two or more blood vessels.
Figure 7B:
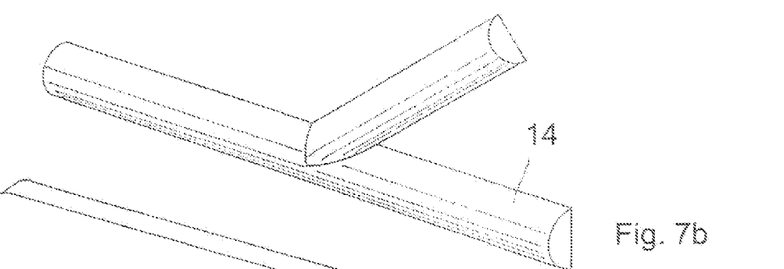
FIGS. 7b and 7c show two possible embodiments of a submould.
Figure 7C:
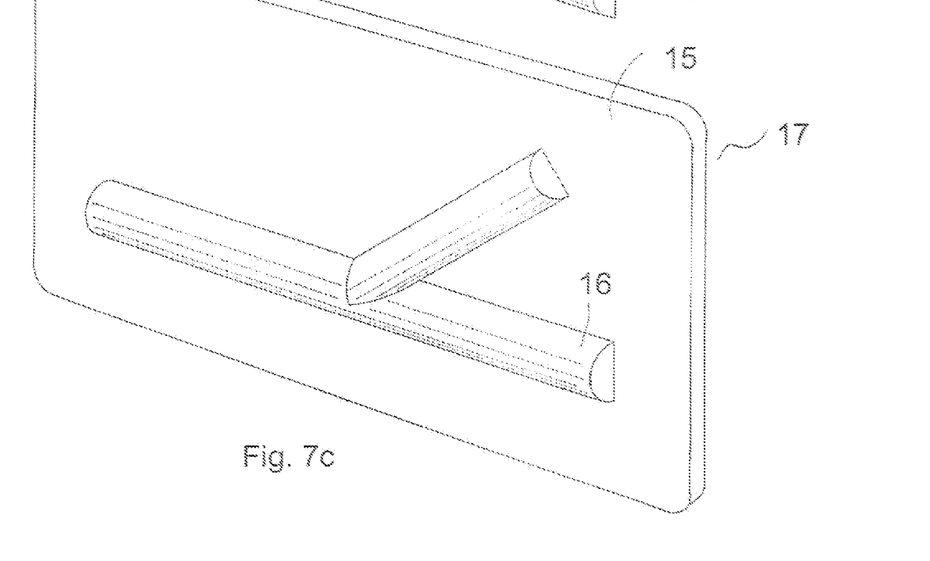

The present invention will now be explained in more detail with reference to the drawings, which show especially preferred embodiments of the present invention. A preform is made, among other things, which preform functions as a mould for a heart valve (FIGS. 4-6). The drawings show a mould for a heart valve comprising three membranes; according to the invention, however, also other types of valves comprising more or fewer membranes can be produced.

FIG. 4a shows three submoulds 1, each comprising one upper surface 2 and two contact surfaces 3, which submoulds are each separately provided with a fibre layer by means of an electro-spinning process. Said three submoulds 1 are so constructed that they substantially exclusively comprise convex surfaces besides the usual flat surfaces. It should be understood that the submould 1 does not have any concave surfaces, so that said electro-spinning will lead to a uniform fibre layer. The submoulds 1 are configured to fit together to form the mould.

FIG. 4b is a sectional view of the three submoulds 1 of FIG. 4a, showing the submoulds after a fibre layer 4 has been applied to each of the individual submoulds 1. The submoulds 1 have subsequently been combined into an assembly 5 by placing the contact surfaces 3 into abutment with each other. The part 6 is called the co-optation surface, which is very important in obtaining a properly functioning artificial heart valve. The fact is that such a co-optation surface ensures that the membranes will correctly butt together after the incubation of the preform with human or animal cells so as to obtain the final biological heart valve. Since a certain degree of shrinkage of the preform may occur during incubation, it is important that an extra edge (the co-optation surface) is present on the membranes, so that said co-optation surfaces 6 can prevent openings being formed between the membranes when shrinkage occurs, which openings might lead to a leaking heart valve. Such a co-optation surface is not obtained if a single mould for a heart valve is used instead of three submoulds 1 according to the present invention.

FIG. 5a shows the assembly 5 of the submoulds 1 provided with a fibre layer (not shown). The assembly 5 is held together by means of a ring construction 7, but it is also possible to use other, conventional methods, of course. Furthermore, a complementary submould 8 is shown, which can be placed on the end of the assembly 5 with a close and precise fit.

The entire mould of the heart valve as shown in FIG. 5b consists of the assembly 5 of the submoulds 1 provided with a fibre layer, a ring construction 7 and the submould 8. In a next step (d) of the method, the entire mould will be provided with a fibre layer 9 by electro-spinning.

FIG. 5c is a sectional view of the mould after step c), showing submoulds 1,8 with upper surfaces 2 and fibre layers 4,9. The figure furthermore shows the co-optation surface 6, which forms part of the fibre layer 4, membranes 10, likewise forming part of the fibre layer 4, which membranes 10 are formed on the upper surfaces 2 of the submoulds 1.

FIGS. 6a and 6b are views of the preform thus obtained after the submoulds 1,8 have been removed. Said submoulds can be carefully removed from the fibre layer(s) one by one. Said removal may take place by hand, for example. In addition, part of the fibre layers 4 on the internal contact surfaces 3 is removed, with the exception of the co-optation surface 6, which is maintained. FIG. 6a is a top plan view and FIG. 6b is a side view of the preform after the submoulds 1,8 have been removed, showing the membranes 10, the fibre layer 4 (full line) and the fibre layer 9 (dotted line), whilst FIG. 6b also shows the co-optation surface 6.

Although the present invention has been explained on the basis of preferred embodiments, it is also possible to use the present invention for producing other preforms to be used in the production of implants for other parts of the body, such as other valves in the heart or blood vessels, or parts of joints, for example a kneecap, and the like.

Additional embodiments are disclosed in the appended claims.

What is claimed is:

1. A multilayer preform obtained by electro-spinning, which preform is suitable as a scaffold for a cardiovascular prosthesis, which preform comprises a layer of fibers with at least one layer of microfibers having a diameter in the range of 3 micrometers to 20 micrometers and at least one layer of nanofibers having a diameter in the range of 50 nanometers to 800 nanometers, wherein the pore sizes within the layer of fibers are in the range of 1 micrometers to 300 micrometers and suitable for cell infiltration and cell ingrowth throughout the thickness of the layer of fibers, wherein the infiltrated and ingrown cells are capable of forming the cardiovascular prosthesis, wherein the fibers in the layer of fibers are biodegradable or bioabsorbable polymeric fibers, and wherein the fibers biodegrade or bioabsorb upon formation of the cardiovascular prosthesis therewith replacing the scaffold and leaving the cardiovascular prosthesis.

2. The preform according to claim 1, wherein the pore size of the at least one layer of microfibers and/or the at least one layer nanofibers is between 5 and 100 micrometers.

3. The preform according to claim 1, wherein the diameter of the microfibers is in the range of 5 micrometers to 18 micrometers.

4. The preform according to claim 1, wherein the diameter of the nanofibers is in the range of 200 nanometers to 700 nanometers.

5. The preform according to claim 1, wherein the porosity of the layer of microfibers and/or the layer of nanofibers is in the range of 70 to 95%.

6. The preform according to claim 1, wherein the cardiovascular prosthesis is a heart valve prosthesis.

* * * * *